United States Patent [19]
Teppke

[11] Patent Number: 5,960,640
[45] Date of Patent: Oct. 5, 1999

[54] CRYOSTATIC MICROTOME

[75] Inventor: Dieter Teppke, Schwetzingen, Germany

[73] Assignee: MICROM Laborgerate GmbH, Germany

[21] Appl. No.: 08/939,270

[22] Filed: Sep. 29, 1997

[30] Foreign Application Priority Data

Sep. 30, 1996 [DE] Germany .................. 196 40 044

[51] Int. Cl.⁶ ............................................. F25C 5/02
[52] U.S. Cl. ................................. 62/320; 83/915.5
[58] Field of Search .................. 62/320; 83/915.5, 83/171

[56] References Cited

U.S. PATENT DOCUMENTS

| | | | |
|---|---|---|---|
| 3,220,290 | 11/1965 | Shandon | 83/915.5 |
| 3,296,821 | 1/1967 | Malinin | 83/915.5 |
| 3,462,969 | 8/1969 | Grasenick et al. | 83/915.5 |
| 4,548,051 | 10/1985 | Moessner . | |
| 4,979,376 | 12/1990 | Biehl et al. | 62/320 |
| 5,048,300 | 9/1991 | Lihl | 83/915.5 |
| 5,533,342 | 7/1996 | Gordon | 62/320 |

FOREIGN PATENT DOCUMENTS

PCT/GB86/00595   4/1987   WIPO .

*Primary Examiner*—Ronald Capossela

[57] ABSTRACT

A cryostatic microtome has a cryostatic chamber, and a microtome arranged in the cryostatic chamber, and including a specimen holder and a knife holder. In order to maintain high dynamics with respect to temperature changes and thereby a rapid matching to changing specimen consistencies, a coolable specimen holder and a coolable knife holder are provided, so that both the temperature of the specimen holder and also the temperature of the knife holder are adjustable independently of each other. Sections of improved quality can be attained by the free and independent temperature adjustment of the knife and specimen.

12 Claims, 3 Drawing Sheets

CRYOSTATIC MICROTOME

BACKGROUND OF THE INVENTION

1. Field of the Invention

The invention relates to a cryostatic microtome, or a microtome cryostat, and more particularly to a cryostatic microtome with a cryostatic chamber and a microtome arranged in the cryostatic chamber, including a specimen holder and a knife.

2. Description of Prior Art

Cryostatic microtomes of the above kind have been known for a long time. They are usually used to cut thin sections from specimens, which are then analyzed under a microscope. For this purpose, cryostatic microtomes have a cooled cryostatic chamber in which a specimen holder is located to receive a specimen to be cut, together with a knife holder that can be moved relative to the specimen holder. A knife that cuts the sections from the specimen is received in the knife holder. Cooling is required in order to cut specimens which have been prepared by freezing. The optimum temperature of the specimens to be cut is determined empirically and is different for specimens of different consistency. The cooling of conventional cryostatic microtomes with a cryostatic chamber takes place in different ways.

In a cryostatic microtome described in U.S. Pat. No. 4,548,051, which is constructed as described above, the cooling is effected by a central cooling device, which cools the air in the cryostatic chamber until the specimen to be cut has reached a suitable temperature.

WO 87/022130 likewise describes a cryostatic microtome as described above. Here the cooling takes place by means of a central cooling device in which the air temperature of the cryostatic chamber is cooled down and by an additional cooling means on the specimen holder in the form of a Peltier element by means of which the temperature of the specimen to be cut can be finely controlled.

Furthermore, cryostatic microtomes are known in the art that operate in ambient air and are not located in a cryostatic chamber. Since the knife and the specimen cannot be cooled by means of a central cooling system in ambient air, as in a closed cryostatic chamber, cooling devices located in both the specimen holder and the knife holder enable the specimen holder and the knife holder to be cooled. In such microtomes, the knife holder, and hence the knife, is cooled to a fixed, predetermined temperature, while the temperature of the specimen in the specimen holder is adjustable. Such cryostatic microtomes usually do not reach particularly low temperatures, because the warm ambient air warms the microtome too much.

SUMMARY OF THE INVENTION

The object of the present invention is a cryostatic microtome of the kind described with a cryostatic chamber with improved properties.

This object is attained by a cryostatic microtome with a cryostatic chamber and a microtome arranged in the cryostatic chamber that includes a coolable specimen holder and a coolable knife holder, in which the temperature of the specimen holder and the temperature of the knife holder are adjustable independently of each other.

According to the invention, both the temperature of the specimen holder and the temperature of the knife holder are adjustable independently of each other. The term "adjustable" is to be understood as meaning that the temperature is selectable by the user within a temperature range and is then adjusted according to the selected temperature by a regulating mechanism.

A series of advantages derive from the invention. It has been shown that the qualities of a section depend on the temperature of the specimen, and quite considerably on the temperature of the knife. Thus the sections of the specimen can be considerably improved by the separate adjustability of the temperature of the knife holder and hence of the knife fixed to it. The respective optimum temperature is set for the specimen holder and for the knife holder and can be different for the knife and the specimen. Furthermore, as was not heretofore known for cryostatic microtomes with a cryostatic chamber, a cooling means is located directly on the knife holder, so that the ambient temperature in the cryostatic chamber no longer has to be kept as low, by a wide margin, as was required in conventional cryostatic microtomes having a cryostatic chamber. This provides the advantage, in particular, that because of a reduced consumption of energy for cooling the chamber, the dimensions of the cooling device can be greatly reduced, with the added advantage of a reduced size of the whole microtome cryostat. Furthermore, the microtome cryostat can put into operation considerably more quickly than the microtome cryostats with a cryostatic chamber of the prior art, since the knife and the specimen do not first have to be cooled by means of the ambient temperature in the chamber, but both are directly cooled.

Different techniques may be used for temperature control of the specimen holder and of the knife holder. The cooling control can, for example, take the form of a well known two-step controller, in which cooling is switched off when the temperature falls below the set temperature and is switched on again when the set temperature is exceeded. Moreover, adjustment of the temperature can also take the form of a knife holder and a specimen holder that can be cooled and heated independently of each other.

For example, one possibility is a Peltier element that is provided in the specimen holder or the knife holder, respectively, as a cooling and heating means. The Peltier elements either heat or cool depending upon the direction of the current applied to the Peltier element. Additionally, small evaporators connected to a cooling device are provided in the knife holder and in the specimen holder, for cooling the Peltier elements.

Since the temperature of the knife usually does not have to be set as low as the temperature of the specimen to be cut, an electrical heating element can be built into the knife holder. This arrangement is more cost favorable, and supplies heat in opposition to the temperature of the evaporator, in a defined manner, for adjustment and/or controlling the temperature of the knife holder.

Although the cooling of the specimen holder and of the knife holder takes place mainly by means of the evaporators mounted on them, it is nevertheless advantageous to provide in the cryostatic chamber an additional evaporator which lowers the air temperature in the cryostatic chamber. The air temperature in the cryostatic chamber can be well above the temperature of the specimen to be cut or of the knife, in contrast to the conventional cryostats with cryostatic chambers.

In order to keep the energy required for cooling the microtome as small as possible, and thus make the size of the cooling device as small as possible, only a few parts of the microtome should be provided in the cryostatic chamber, so that there are fewer parts to be cooled, and the cryostatic chamber can be kept small. Electrical components which can contribute heat to the cryostatic chamber, such as, for example, electric motors and the like, are arranged outside the cryostatic chamber. The microtome is thus arranged partially inside and partially outside the cryostatic chamber. In order to insure that as little cold as possible can flow out between the parts lying within the cryostatic chamber and the parts lying outside the cryostatic chamber, and at the same time to insure the highest possible stability of the microtome, components of VA steel should exclusively be used in the transition region between parts of the microtome lying inside the cryostatic chamber and parts of the microtome lying outside the cryostatic chamber.

The cryostatic microtome can be used particularly advantageously when the specimen holder and the knife holder are cooled to the set working temperature in a very short time. This is particularly possible when two cooling circuits are provided in the cooling device, the second cooling circuit, to which the evaporators in the specimen holder and in the knife holder are connected, being precooled by means of a first cooling circuit via a coaxial heat exchanger.

BRIEF DESCRIPTION OF THE DRAWINGS

Preferred embodiments of the invention will now be described, taken together with the drawings, in which.

DETAILED DESCRIPTION OF PREFERRED EMBODIMENTS

Figure 1:
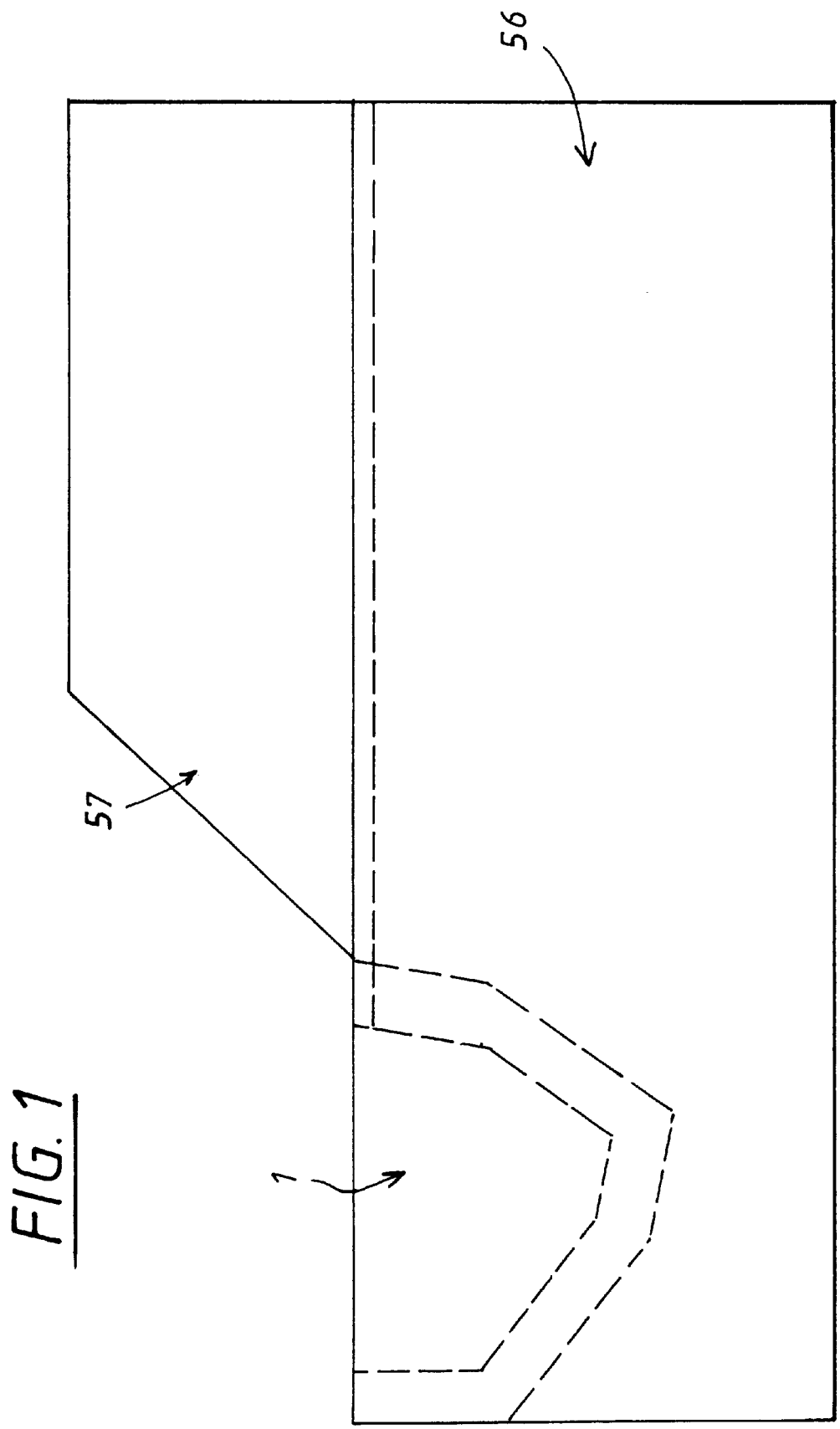
FIG. 1 shows a simple schematic side view of the cryostatic microtome.

FIG. 1 shows a simple schematic side view of the cryostatic microtome according to the invention, from which the contour of the cryostatic microtome and the division of the cryostatic microtome can be gathered. The reference numeral (1) denotes the cryostatic chamber, (57) denotes the chamber to receive the electronic control and regulating components, and (56) denotes the chamber to receive important components of the cooling device.

Figure 2:
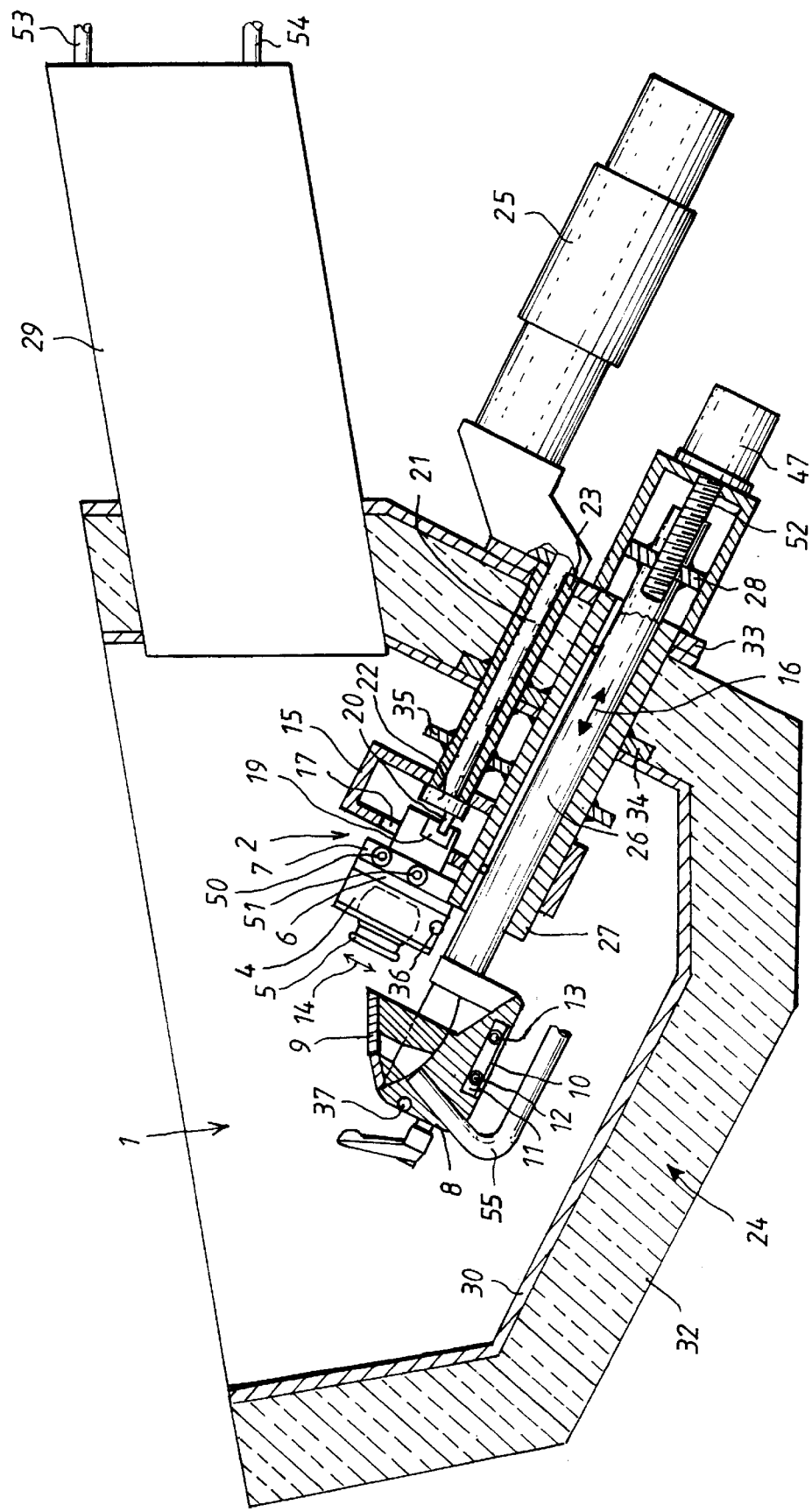
FIG. 2 shows a partial section through the cryostatic microtome according to FIG. 1.

FIG. 2 shows a partial section, not to scale, of a cryostatic microtome according to FIG. 1, with a cryostatic chamber (1) with a microtome (2) arranged therein, the representation being essentially limited to the purely mechanical components of the microtome (2). Details such as, for example, electrical leads, cooling device connections, etc., are largely omitted. The microtome (2) includes a coolable specimen holder (4) on which the specimen (5) to be cut is fastened. A small evaporator (7) is provided in the specimen holder (4) to cool the specimen holder (4), and is connected by connections (50, 51) to a cooling device, described hereinbelow. The small evaporator (7) supplies the temperature without further regulation, so that a Peltier element (6) is additionally mounted on the evaporator (7) and can provide additional cooling or heating, depending on the direction of a current which is applied to it. The temperature of the specimen holder can be very finely adjusted in this manner, corresponding to the requirements for the specimen (5) which is to be cut.

In addition, the microtome (2) also has a coolable knife holder (8). The knife holder (8) serves to receive a knife or a disposable blade (9). The specimen holder (4), with the specimen (5) fastened to it, is moved relative to the cutting edge of the knife or the disposable blade (9), in order to cut thin slices from the specimen (5). The exact mechanism for carrying out this process will be explained more precisely hereinbelow.

An evaporator (10), is provided in the lower region of the knife holder (8) for cooling the knife holder (8) and is connected to a cooling device via connections (12, 13). The evaporator (10) cools the knife holder (8), and thereby the knife or disposable blade (9), to as constant as possible a temperature value. Since the temperature which can be attained is sufficient for all selectable temperatures of the knife or of the blade (9), the temperature is adjusted solely by an electrical heating element (11) beneath the evaporator in the knife holder (8). To adjust the temperature of the knife holder (8), the heating power of the heating element (11) is simply raised until the knife holder (8) has the desired temperature.

Thus both the temperature of the specimen holder (4) and the temperature of the knife holder (8) are adjustable independently of each other. For adjustment of the temperature, the knife holder (8) and the specimen holder (4) can be cooled, independently of each other, by means of the evaporators (7, 10) or of the Peltier element (6), and also can be heated by the Peltier element (6) and the heating element (11). A temperature sensor (36, 37) is provided in the knife holder (8) and the specimen holder (4), so that the actual temperature of the specimen holder (4) in the region of the specimen, and of the knife holder (8) in the region of the knife or blade holder (9), can be separately measured. The temperatures of the specimen holder (4) and knife holder (8) are controlled by means of a control device (not shown) to respective predetermined reference temperatures, which in general are different for the specimen holder (4) and for the knife holder (8). The temperature values measured by the temperature sensors (36, 37) correspond to the respective reference temperatures. The temperature in the cryostatic chamber itself is however not separately regulated.

The precise mechanism of the microtome, by which the specimen holder (4), and thus the specimen (5) arranged on it, is moved relative to the knife or blade holder (9) of the knife holder (8) will now be described with reference to FIG. 2. To cut the specimen (5), the specimen holder (4) is moved up and down, corresponding to the double arrow (14). For this purpose, the specimen holder (4) is movably guided in the direction of the arrow (14) between two side portions (15), of which only one is shown here, and which form a chassis. For this purpose, the side portions (15) respectively have on their inner wall a V-shaped groove (17) in which rollers run. The rollers are attached to the specimen holder (4) and are not shown in detail here. The rollers are arranged on the specimen holder (4) such that alternately a respective roller runs on one shank of the V-groove and also a roller lying below it runs on the other shank of the V-groove, and so on. Such guides are known to one skilled in the art under the term cross roll guidance, and will not be further described here. A horizontal groove (19) is present on the back side of the specimen holder (4), and serves for the up and down motion of the specimen holder (4). A sliding block is guided, displaceable horizontally, in the groove (19). A projection (20) of a lever (22) on a rotatable shaft (21) engages in a hole through the sliding block. When the shaft (21) turns, a horizontal motion of the sliding block in the groove (19) results from the horizontal component of motion of the lever (22), and a vertical motion of the specimen holder (4) results from the vertical component of motion of the lever.

As can be seen from FIG. 2, the shaft (21) is set in rotation by a drive (25) which is located outside the cryostatic chamber (1). For this purpose, the shaft (21) is rotatably guided in a sleeve (23), which passes through the insulating wall (24) of the cryostatic chamber (1). The drive (25) can be constructed, as shown in FIG. 1, in the form of an electric motor, or else in the form of a handwheel drive which is driven by a handwheel fitted to the side of the cryostatic microtome.

The feed motion of the knife or blade holder (9) in the direction of the arrow (16) takes place as follows. The knife holder (8) is movably guided on two tubes (26) lying one behind the other, only the rear one being shown here, by means of corresponding guides in the sleeves (27), in the direction of the arrow (16). As can also be seen here, the knife holder is located in the cryostatic chamber (1), while the other end of the tubes (26) are located outside the cryostatic chamber. For moving the knife holder (8) in the direction of the arrow (16), the tubes (26) are connected by a bridge (28), and a nut, not shown in detail here, is present in the middle of the bridge. The nut is connected to a threaded spindle (52) which is driven by a stepping motor (47). To displace the knife holder (8) in the direction of the arrow (16), the threaded spindle (52) is simply turned by the stepping motor (47), so that the nut screwed on the threaded spindle moves the bridge back and forth along the arrow (16). The position of the stepping motor (47) and the nut can be interchanged, so that the stepping motor is located on the bridge (28), and the nut is seated where the stepping motor (47) is shown in FIG. 2.

The microtome itself is arranged on the obliquely inclined back wall of the cryostatic chamber such that the direction of motion for the feed motion of the knife carrier is obliquely upward or downward. At the same time, the constructional height is chosen so that a free space of 5 to 10 cm remains between the lowest microtome components and the floor of the cryostatic chamber, so that cutting waste can easily be cleaned from the cryostatic chamber.

A plate evaporator (29) in the cryostatic chamber (1) cools the air temperature of the cryostatic chamber (1), in addition to the evaporators arranged in the knife holder (8) and in the specimen holder (4). Since the knife holder (8) and the specimen holder (4) are separately cooled, the plate evaporator (29) can be dimensioned relatively small, since the air temperature in the cryostatic chamber (1) no longer has to correspond to the temperature of the specimen holder (4) or of the knife holder (8). While the air temperature of the cryostatic chamber in conventional cryostatic microtomes is cooled down to −55° or even −60° centigrade, it is sufficient in the cryostatic microtome according to the invention to cool the air temperature to −20° centigrade. The knife holder can then, at an air temperature of −20° centigrade, assume a temperature of −35° centigrade, and the specimen holder (4) can even be cooled by the Peltier element as low as −55° centigrade. As mentioned above, energy is thereby saved, which is reflected in a substantially smaller cooling device and a substantially smaller cryostatic microtome. A further advantage of the direct cooling of the specimen holder (4) and of the knife holder (8) is that higher air temperatures in the cryostatic chamber (1) have less disadvantageous effects on the quality of the sections. The distance of the microtome to the upper edge of the cryostatic chamber can therefore also be designed to be small, which again favors the ergonomics.

In order to further reduce the required cooling power, the cryostatic chamber (1) is well heat-insulated by a cryostatic wall (24). The cryostatic wall (24) consists of a sheet metal trough (30) of VA steel, which is surrounded by a foam material layer which provides good heat insulation. In addition, the cryostatic chamber (1) is covered by a sheet of plastic or glass, not shown here. Furthermore, large portions of the microtome (2) are arranged outside the cryostatic chamber (1), so that on the one hand the cryostatic chamber (1) is as small as possible and on the other hand as few portions as possible of the microtome are to be cooled as well. Electrical components in particular, such as for example the stepping motor (47) or the drive (25), are arranged outside the cryostatic chamber (1), in order to prevent heating by waste heat radiated by these components. Since the microtome (2) is arranged partially inside and partially outside the cryostatic chamber (1), VA steel is exclusively used in the components of the microtome (2) arranged in the transition region between the components (portions) arranged within the cryostatic chamber (1) and the components (portions) arranged outside the cryostatic chamber (1). The rods (26), the sleeves (27), the shaft (21) and the sleeve (23) are thus made of VA steel. The choice of this material has the particular advantage that on the one hand a material of very low thermal conductivity is used, which on the other hand, has a very high rigidity.

In order to increase the rigidity of the whole microtome (2) still further, the sleeves 27 and the sleeve 23 are further reinforced by means of bridges (33, 34, 35).

Figure 3:
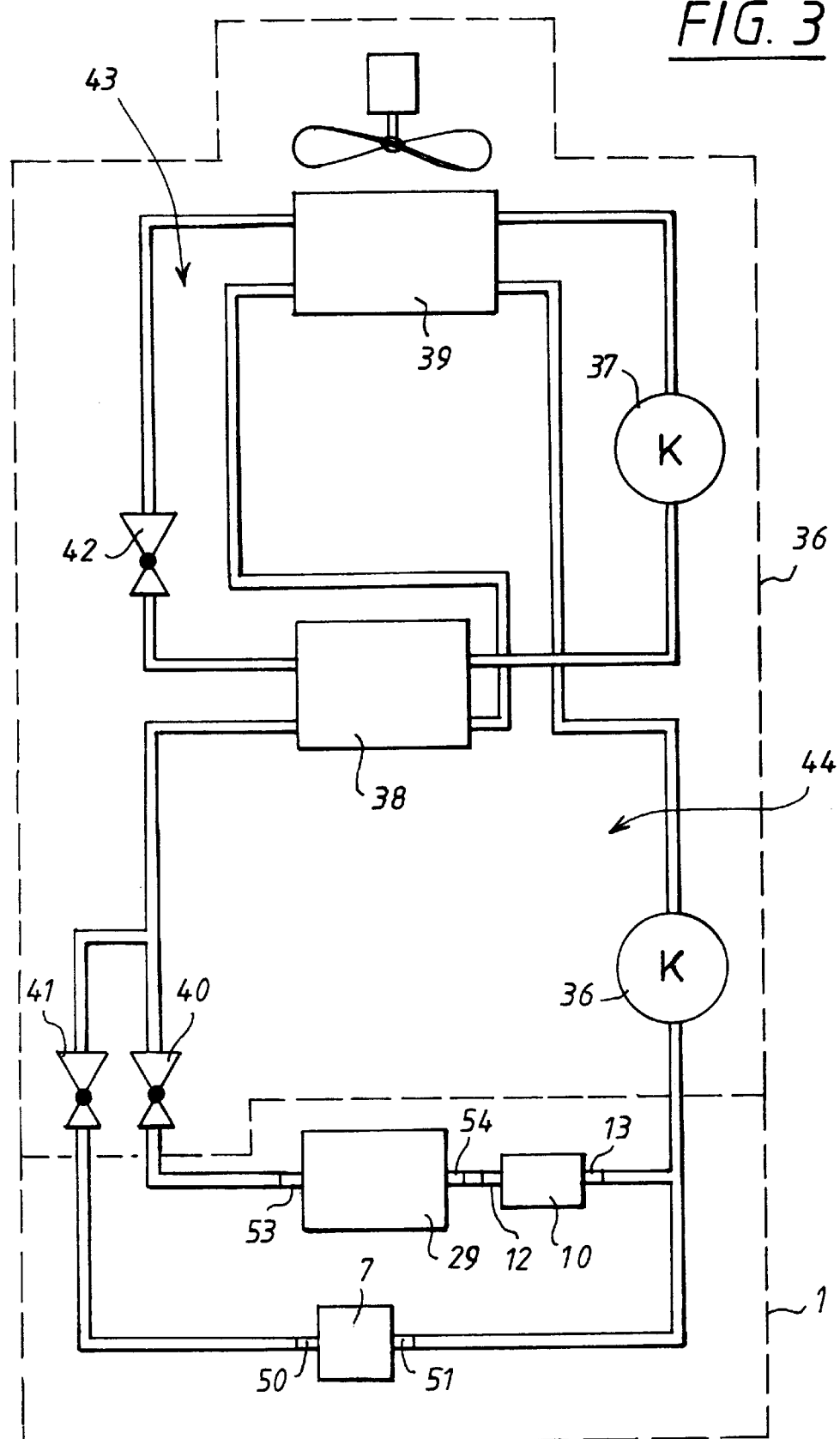
FIG. 3 shows a block circuit diagram of the cooling device of microtomes according to FIG. 1.

The cooling device of the cryostatic microtome will now be described with reference to FIG. 3; portions of the cooling device are located in the cryostatic chamber (1), and other portions are located in the chamber (56) of the cryostatic microtome (see FIG. 1). Strictly speaking, the cooling device shown comprises two serially connected cooling circuits (43, 44), in which the first cooling circuit (43) serves for pre-cooling and the second cooling circuit (44) then runs via the evaporators (7, 10) in the specimen holder (4) and in the knife holder (8), and also via the plate evaporator (29). The first cooling circuit (43) has a liquefier (39), which runs via a throttle (42) or a capillary into a coaxial heat exchanger (38) and, via a compressor (37), runs back into the liquefier (39). The coolant for the second cooling circuit, still to be described, is pre-cooled in the coaxial heat exchanger (38) by the first cooling circuit (43). The coaxial heat exchanger (38) then acts like an evaporator for the first cooling circuit, cooling the evaporating coolant in the second cooling circuit (44). The second cooling circuit (44) is constructed similarly to the first. As is usual in refrigerators, throttles (40, 41) or capillaries are provided, the outlet of which is then connected to the plate heat exchanger (29) and the evaporator (10) in the knife carrier (8), or to the evaporator (7) in the specimen holder (4). The outlets of the evaporators (7, 10) are likewise connected to a compressor (36), which then pumps the compressed, vapor-phase coolant to the liquefier (39). The two-part cooling circuit just described has the particular advantage that the second cooling circuit (44) is already pre-cooled. Because of this, the cryostatic chamber (1) or the cryostatic microtome (2) can be cooled to the working temperature within a relatively short time. Furthermore, the cryostatic microtome can be switched over relatively easily into a standby mode in which only the cooling circuit (43) still runs for pre-cooling the coaxial heat exchanger (38). The cooling circuit (44) can be switched off in the standby mode.

The evaporators (7, 10) are thus components of a cooling circuit which has a coaxial heat exchanger (38). Furthermore, the cooling circuit is designed such that the liquefier (39) and at least one of the compressors (36, 37) is located at the height of the cryostatic chamber (1) behind the cryostatic chamber (1). This has the particular advantage that a relatively compact cryostatic microtome can be provided, which is easily transportable and can be arranged on a table without giving rise to problems.

It should also be noted that the evaporator (7) in the specimen holder, on the one hand, and the evaporator (10) in the knife holder and the plate evaporator (29) on the other hand, are arranged in two parallel-connected partial circuits of the second cooling circuit (44), which respectively have their own throttle (40, 41). Thus fewer pressure problems arise in contrast to single-circuit cooling circuits in which all the evaporators are connected in series. Furthermore a lower minimum temperature results by means of the separate partial circuit for the evaporator (7) in the specimen holder. Since the temperature of the knife and of the cryostatic chamber can as a rule be higher than the specimen temperature, the associated evaporators (10, 29) are connected in series. The partial circuits for all three evaporators can however be separate, if a somewhat greater cost is allowed for, and they can respectively have their own throttle.

The cryostatic microtome can advantageously also have connections by which it can be coupled to external accessory devices. Thus, for example, the knife holder has a suction device (55), only partially shown in FIG. 2, by means of which the cutting waste which arises when cutting the specimen (5) to be sectioned is sucked away. For the use of this device, a connector which is connected to the suction device (55) (and which is not shown in detail here) can be provided on the underside of the cryostatic microtome, and can be connected to a device which produces a reduced pressure. The reduced pressure sucks out the cutting waste via the suction device (55) on the knife holder (8). Likewise, a connection can be provided on the underside of the cryostatic microtome, through the use of which the cryostatic chamber of the cryostatic microtome can be disinfected.

The invention is in no way limited to the preferred embodiments shown and described herein. All modified embodiments are also included. For example, the cooling circuit can be arranged as a single cooling circuit, so that the throttle (42), the coaxial heat exchanger (38) and the compressor (37) can be omitted. Likewise, for example, the mechanism of the microtome that carries-out the cutting motion can be designed quite differently.

I claim:

1. A cryostatic microtome, comprising:
   a cryostatic chamber,
   a microtome including a specimen holder and a knife holder,
   at least said specimen holder and said knife holder being arranged within said cryostatic chamber,
   a first cooling element within said specimen holder, and
   a second cooling element within said knife holder,
   said specimen holder and said knife holder being cooled directly and independently of each other.

2. The cryostatic microtome according to claim 1, further comprising a regulating mechanism providing selection of a first temperature for said specimen holder and selection of a second temperature for said knife holder, whereby different temperature values are selected for said first temperature and for said second temperature respectively, said regulating mechanism further providing a temperature adjustment of said specimen holder to said first temperature and a temperature adjustment of said knife holder to said second temperature.

3. The cryostatic microtome according to claim 2, further comprising a cooler to cool said cryostatic chamber to a third temperature, said first temperature and said second temperature being lower than said third temperature.

4. The cryostatic microtome according to claim 1, said specimen holder and said knife holder each comprising a heating element.

5. The cryostatic microtome according to claim 1, in which said first cooling element comprises a first evaporator arranged within a body portion of said specimen holder and said second cooling element comprises a second evaporator arranged within a body portion of said knife holder.

6. The cryostatic microtome according to claim 5, comprising a third evaporator within said cryostatic chamber.

7. The cryostatic microtome according to claim 5, wherein said microtome is arranged partially inside and partially outside said cryostatic chamber and only VA steel is used in components in a transition region between portions of said microtome that are arranged within said cryostatic chamber and portions of said microtome that are arranged outside said cryostatic chamber.

8. The cryostatic microtome according to claim 5, in which said specimen holder further comprises a peltier element arranged within said body portion of said specimen holder.

9. A cryostatic microtome, comprising:
   a cryostatic chamber,
   a microtome including a specimen holder and a knife holder, at least said specimen holder and said knife holder being arranged within said cryostatic chamber,
   at least one evaporator arranged within said cryostatic chamber,
   a cooling device connected to said at least one evaporator, said cooling device comprising a first cooling circuit and a second cooling circuit each comprising a coolent, and
   a coaxial heat exchanger connected to said first cooling circuit, said coaxial heat exchanger precooling said coolant of said second cooling circuit,
   said second cooling circuit being connected to said at least one evaporator.

10. The cryostatic microtome according to claim 9, in which said at least one evaporator comprises a first evaporator arranged within a body portion of said specimen holder and a second evaporator arranged within a body portion of said knife holder.

11. The cryostatic microtome according to claim 10, in which said second cooling circuit comprises a first and a second partial cooling circuit, each of said partial cooling circuits having a separate throttle, said first and second evaporators being connected to different ones of said partial cooling circuits.

12. The cryostatic microtome according to claim 11, further comprising a third evaporator serially connected to said second evaporator.

* * * * *